United States Patent [19]  
Umezawa et al.

[11] 3,948,882  
[45] Apr. 6, 1976

[54] PROCESS FOR THE PRODUCTION OF A 1-N((S)-α-HYDROXY-ω-AMINOACYL)-3',4'-DIDEOXYNEAMINE OR -3',4'-DIDEOXYRIBOSTAMYCIN

[75] Inventors: Hamao Umezawa; Sumio Umezawa, both of Tokyo; Eiichi Akita, Kamakura; Yukio Horiuchi, Yokohama; Shuntaro Yasuda, Yokohama; Osamu Tsuchiya, Yokohama, all of Japan

[73] Assignee: Zaidan Hojin Biseibutsu Kagaku Kenkyu Kai, Tokyo, Japan

[22] Filed: July 17, 1974

[21] Appl. No.: 489,243

[30] Foreign Application Priority Data  
Aug. 1, 1973  Japan................................ 48-85885

[52] U.S. Cl. 260/210 AB; 260/210 K; 260/210 NE; 424/180
[51] Int. Cl.² ........................................... C07G 3/00
[58] Field of Search...... 260/210 AB, 210 R, 210 K, 260/210 NE

[56] References Cited
UNITED STATES PATENTS
3,792,037   2/1974   Kawaguchi et al........... 260/210 AB

OTHER PUBLICATIONS

Barton, J. W., "Protection of N—H Bond ect," p. 50, *Protective Gps in Org. Chem.* McOmie, Plemum Press, NY, 1973.

Wazner and Zook, *Syn. Org. Chem.*, p. 567, parag. 349, Wiley & Sons, N.Y. 1953.

Adams et al., *Organic Reactions*, Vol. 12, pp. 172–173, 1962, Wiley and Sons, Inc. New York.

Moore et al., Asaserine, "Synthetic Studies I," J.A.C.S. Vol. 76, p. 2884 (1954).

*Primary Examiner*—Johnnie R. Brown
*Assistant Examiner*—Cary Owens
*Attorney, Agent, or Firm*—Larson, Taylor and Hinds

[57] ABSTRACT

Process of producing a 1-N-((S)-α-hydroxy-ω-aminoacyl)-3',4'-dideoxyneamine or -3',4'-dideoxyribostamycin, a useful semi-synthetic antibiotic in which the corresponding 6-O-((S)-α-hydroxy-ω-aminoacyl)-3',4'-dideoxyneamine or -3',4'-dideoxyribostamycine undergoes the acyl-migration reaction by treating with a basic medium.

2 Claims, No Drawings

PROCESS FOR THE PRODUCTION OF A 1-N((S)-α-HYDROXY-ω-AMINOACYL)-3',4'-DIDEOXYNEAMINE OR -3',4'-DIDEOXYRIBOSTAMYCIN

This invention relates to a process for the production of a 1-N-((S)-α-hydroxy-ω-aminoacyl)-3',4'-dideoxyneamine or -3',4'-dideoxyribostamycin which is useful for the treatment of various bacterial infections. More particularly, this invention relates to a process for the production of 1-N-((S)-α-hydroxy-γ-amino-n-butyryl)-3',4'-dideoxyneamine or -3',4'-dideoxyribostamycin.

Kanamycins and neamine (that is, neomycin A) are well known aminoglycosidic antibiotics, and ribostamycin is also a known aminoglycosidic antibiotic, originally designated vistamycin or Antibiotic SF-733 (see the "Journal of Antibiotics" Vol. 23, No. 3, pages 115–161 and No. 4, pages 173–183 (1970)). Ribostamycin has been identified as 5-0-β-D-ribofuranosylneamine. These aminoglycosidic antibiotics have widely been used as valuable, chemotherapeutic agents, but many drug-resistant strains which are resistant to these known antibiotic have occurred in recent years. In these circumstances, the mechanism of resistance of the drug-resistant bacteria to the known aminoglycosidic antibiotics has been studied. For instance, one of the present inventors, H. Umezawa et al. have found that some R-factor carrying strains of gram-negative bacteria, *Staphylococcus aureus* and *Pseudomonas aeruginosa* isolated from patients are resistant to the action of kanamycins and that these kanamycin-resistant strains have the mechanism of resistance that they produce an enzyme capable of phosphorylating the 3'-hydroxyl group of kanamycins and inactivate the kanamucins with aid of this phosphorylating enzyme (see the "Science" Vol. 157, page 1559 (1967)).

On the basis of this finding, H. Umezawa et al have prepared semi-synthetically 3'-deoxykanamycin and 3',4'-dideoxykanamycin B wherein the 3'-hydroxyl group of the kanamycin molecule has been removed therefrom, as well as 3',4'-dideoxyneamine and 3',4'-dideoxyribostamycin (namely, 3',4'-dideoxyvistamycin) as described in the "Journal of Antibiotics" Ser. A, Vol. 21, pages 274–275 (1971); Vol. 24, pages 485–487; Vol. 24, pages 711–712 (1971) and Vol. 25, pages 613–617 (1972). 3'-deoxykanamycin; 3',4'-dideoxykanamycin B; 3',4'-dideoxyneamine and 3',4'-dideoxyribostamycin are actually effective against the above-mentioned kanamycin-resistant strains, but these deoxy-derivatives have now been found to be practically inactive against another kind of kanamycin-resistant strains such as *Escherichia coli* JR66/W677 which has been isolated from another patients. H. Umezawa et al. have found that the latter kind of the kanamycin-resistant strains has the mechanism of resistance that they produce an enzyme capable of adenylylating the 2''-hydroxyl group of the kanamycin or 3',4'-dideoxykanamycin molecule with ATP (adenosine triphosphate) and inactivate kanamycin and 3',4'-dideoxykanamycin through the action of this adenylylating enzyme (see the "Journal of Antibiotics" Vol. 24, pages 911–913 (1971)). Furthermore, it has been found that a class of the drug-resistant gram-negative bacteria such as R-factor carrying strains of *Escherichia coli* for example, *Escherichia coli* JR66/W 677 and LA290R55 has the mechanism of resistance that it produces an enzyme capable of nucleotidylating the 2''-hydroxyl group of kanamycin A and 3',4'-dideoxykanamycin B molecule and inactivates the kanamycin and 3',4'-dideoxykanamycin B with aid of this enzyme (see the "Journal of Antibiotics" Vol. 25, page 492 (1972)).

On the other hand, it is known that butirosin B which is an aminoglycosidic antibiotic produced by a microorganism Streptomyces species is active against some kanamycin-resistant bacteria as well as against some ribostamycin-resistant bacteria. Butirosin B has been identified as 1-N-((S)-α-hydroxy-γ-amino-n-butyryl)-ribostamycin (see the "Tetrahedron Letters" Vol. 28, page 2125 and pages 2617-2630 (1971) and German "Offenlegungsschrift" No. 1914527). From comparison of the antibacterial activity of ribostamycin with that of butirosin B, it has been appreciated that the (S)-α-hydroxy-γ-amino-butyryl substituent at the 1-amino group of the butirosin b molecule has an important role in enabling the ribostamycin to be active even against the ribostamycin-resistant and -sensitive strains and that the presence of the (S)-α-hydroxy-γ-amino-butyryl substituent at the 1-amino group of the butirosin B molecule results in such a steric hindrance of the butirosin B molecule owing to which the butirosin B can be prevented from being inactivated by the attack of the various inactivating enzymes which are produced by the kanamycin-resistant strains of ribostamycin-resistant strains.

On the basis of these findings, H. Umezawa et al. have synthetized 1-N-((S)-α-hydroxy-ω-aminoacyl) derivatives of neamine, 3',4'-dideoxyneamine, ribostamycin or 3',4'-dideoxyribostamycin and have found that these compounds exhibit usefully high antibacterial activity against the drug-resistant bacteria (see co-pending U.S. patent application Ser. No. 402,085; British patent application No. 46,397/73; German patent application No. P 23 50169.1 and French patent application No. 73 36291, as well as the "Journal of Antibiotics" Vol. 26, pages 304–309 (May, 1973)). Accordingly, we have made our further research in an attempt to exploit a new efficient process according to which a 1-N-((S)-α-hydroxy-ω-aminoacyl)-3',4'-dideoxyneamine or -3',4'-dideoxyribostamycin can be synthetized in a facile way and in a favorable yield.

3',4'-dideoxyneamine and 3',4'-dideoxyribostamycin may be represented by a general formula (I):

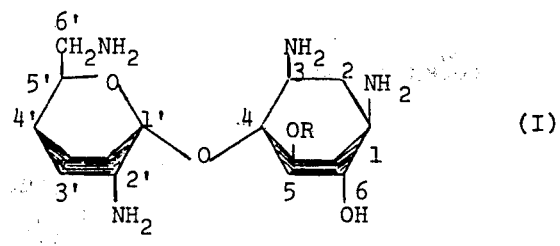

(I)

wherein R is a hydrogen atom or β-D-ribofuranosyl group of the formula

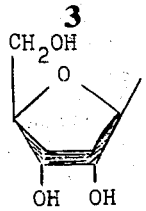

3',4'-dideoxyneamine is shown by the above general formula (I) when R is a hydrogen atom, and 3',4'-dideoxyribostamycin is shown by the above general formula (I) when R is a β-D-ribofuranosyl group (see the "Journal of Antibiotics" Vol. 24, pages 711–712 (1971) and Vol. 25, pages 613–616 (1972)).

An object of this invention is to provide a new route according to which a 1-N-((S)-α-hydroxy-ω-aminoacyl)-3',4'-dideoxyneamine or -3',4'-dideoxyribostamycin of a general formula (II):

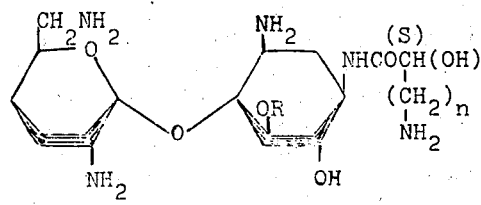

(II)

wherein R is a hydrogen atom or β-D-ribofuranosyl group and n is a whole number of 1 to 4 inclusive, in a relatively facile way and in an improved yield, and in which the corresponding 6-0-((S)-α-hydroxy-ω-aminoacyl)-3',4'-dideoxyneamine or -3',4'-dideoxyribostamycin is at first prepared by esterifying the 6-OH group of the 3',4'-dideoxyneamine or 3', 4'-dideoxyribostamycin with the (S)-hydroxy-ω-aminoalkanoic acid or a reactive derivative thereof and is then subjected to the action of an alkaline medium so as to cause the (S)-α-hydroxy-ω-aminoacyl substituent $$-\overset{(S)}{COCH(OH)(CH_2)_nNH_2}$$

to migrate from the 6-OH group to the 1-NH$_2$ group of the 3', 4'-dideoxyneamine or 3', 4'-dideoxyribostamycin. The symbol (S) shown in the formula (II) is an expression of the steric configuration of organic compounds (see R. S. Cahn, C. K. Ingold & V. Prelog; "Experitia" Vol. 12 pages 81–94 (1956). A further object of this invention is to provide a new process for the production of 1-N-((S)-α-hydroxy-γ-amino-n-butyryl)-3', 4'-dideoxyneamine or -3', 4'-dideoxyribostamycin which may be carried out in a relatively facile way and gives the desired product in an improved yield. Another objects of this invention will be clear from the following descriptions.

According to this invention, there is provided a process for the production of a 1-N-((S)-α-hydroxy-ω-aminoacyl)-3', 4'-dideoxyneamine or -3', 4'-dideoxyribostamycin of the formula (II):

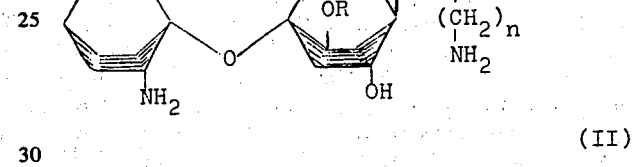

(II)

wherein R is a hydrogen atom or β-D-ribofuranosyl group of the formula

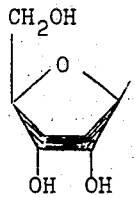

and n is a whole number of 1 to 4, which comprises subjecting a 6-0-(((S)-α-hydroxy-ω-aminoacyl)-3', 4'-dideoxyneamine or -3', 4'-dideoxyribostamycin of the formula (III):

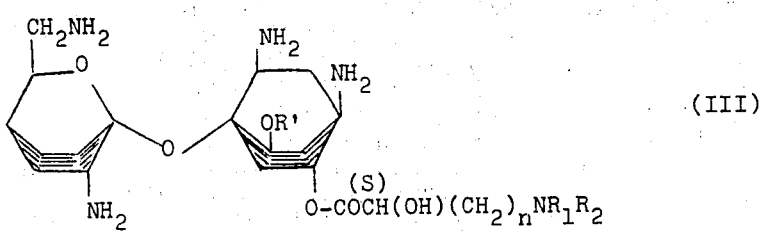

(III)

wherein R' is a hydrogen atom, a known hydroxyl-protecting group such as an acyl group or a β-D-ribofuranosyl group of the formula

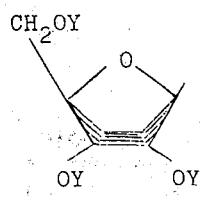

where each Y is independently a hydrogen atom or a known hydroxyl-protecting group such as an acyl group, for example, an alkanoyl group of 2–6 carbon atoms (e.g., acetyl, propionyl or butyryl), an aminoalkanoyl group of 2–6 carbon atoms (e.g., β-hydroxyl-γ-amino-n-butyryl), benzoyl, benzyl, methoxycyclohexyl or cyclohexylidene; and $R_1$ and $R_2$ may be the same or different and each is independently a hydrogen atom or a known amino-protecting group selected from an acyl group such as an alkanoyl group of 2–6 carbon atoms (e.g., acetyl, propionyl or butyryl), an alkoxycarbonyl group such as an alkoxycarbonyl group of 2–5 carbon atoms (e.g., methoxycarbonyl, ethoxycarbonyl, propoxycarbonyl or butoxycarbonyl), an aralkyloxycarbonyl group such as phenylalkyloxycarbonyl group containing the alkyl group of 1–4 carbon atoms (e.g., benzyloxycarbonyl) or an aryloxycarbonyl group (e.g., phenyloxycarbonyl or naphthyloxycarbonyl); or $R_1$ and $R_2$ taken together forms a phthaloyl group; and $n$ is a whole number of 1 to 4, to the action of a basic medium to produce an acyl-migration product of the formula (IV):

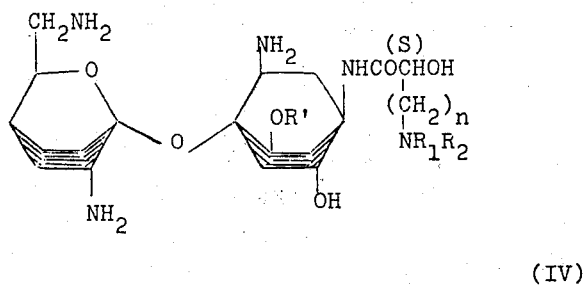

wherein R', $R_1$, $R_2$ and $n$ have the same meanings as defined above, and if at least one of the amino-protecting and hydroxyl-protecting groups remain in the acyl-migration product removing the amino-protecting group and the hydroxyl-protecting group from the acyl-migration product (IV), to give the desired product (II).

In carrying out the process of this invention, the starting compound 6-0-((S)-α-hydroxyl-ω-aminoacyl)-3', 4'-dideoxyneamine or -3', 4'-dideoxyribostamycin (III) may be subjected to the action of the basic or alkaline medium by treating the starting compound in solution in water or an organic solvent under basic or alkaline conditions which are provided by the presence of an organic base such as tertiary amine, for example, triethylamine or hydrazine or an inorganic base such as an alkali metal hydroxide, for example, sodium or potassium hydroxide or carbonate or a basic anion-exchange resin in such a quantity enough to give the basicity or alkalinity to the solution of the starting compound. This basic treatment may be done simply by dissolving the starting compound in a solvent therefore but containing a base in an amount sufficient to make the solution basic or by adding to a solution of the starting compound a base in an amount sufficient to make the solution basic, and then by heating the basic solution of the starting compound at an elevated temperature, preferably at a temperature of 50°–100°C. As the organic solvent which may be used as the reaction medium for the basic treatment of the present process, there may be mentioned a lower alkanol of 1–4 carbon atoms, for example, methanol, ethanol, butanol and propanol, either aqueous or anhydrous. When the starting compound of the formula (III) is subjected to the action of the basic medium in this way, there takes place such a reaction of rearrangement wherein the group $-COCH(OH)(CH_2)_nNR_1R_2$ bonded through the ester-linkage to the hydroxyl group in the 6-position of the 3', 4'-dideoxyneamine or 3',4'-dideoxyribostamycin molecule of the starting compound is liberated therefrom and transferred to the amino group in the adjacent 1-position of said molecule, producing the acyl-migration product of the formula (IV).

This reaction of rearrangement, that is, the reaction in which such an acyl group having been bonded through the ester-linkage to a hydroxyl substituent on a carbon atom of an organic compound molecule is caused to transfer from said hydroxyl group to such an amino substituent which is existing on a carbon atom adjacent to the first-mentioned carbon atom and in the "trans"-position in relation to said hydroxyl group, by making alkaline or basic the conditions of the environment medium wherein the organic compound molecule is present, is the new reaction which was previously discovered by the present inventors (see co-pending U.S. patent application Ser. No. 390,217; British patent application No. 39735/73; German patent application No.P 23 42946.1 and French patent application No. 73 30875, as well as the "Journal of Antibiotics" Vol. 26, pages 365–367 (1973)). This new reaction which was discovered by the present inventors is utilized in the process of this invention.

It is known that, in general, an acyl group is likely to be bonded to a hydroxyl group under acidic conditions but is likely to be bonded to an amino group under basic conditions, so that the acyl group migrates from the hydroxyl group to the amino group when the nature of the environment medium containing the aforesaid different groups is reversed from acidicity to basicity, and vice versa. This phenomena is known as "acyl migration" (see "Organic Reactions" Vol. 12, page 173, published from John Wiley & Sons, 1962). However, the acyl migration has never been utilized before the process of this invention for the purpose of introducing the acyl group in to an amino group existing in a particular position of a molecule when said molecule bears many amino groups.

In carrying out the process of this invention, the migration of the (S)-α-hydroxy-ω-aminoacyl group $-COCH(OH)(CH_2)_nNR_1R_2$ takes place from the 6-hydroxyl group to the 1-amino group of the 3', 4'-dideoxyneamine or 3', 4'-dideoxyribostamycin molecule of the starting compound (III) under the basic conditions. When the amino-protecting groups $R_1$ and $R_2$ as well as the hydroxyl-protecting group Y which are possibly present in the starting compound (III) are such ones which are cleavable under the basic conditions, for example, an acyl group, a partial or complete removal of such kind of the amino-protecting group and the hydroxyl-protecting group would occur concurrently with the reaction of migrating the (S)-α-hydroxy-ω-aminoacyl substituent from the 6-hydroxyl group to the 1-amino group takes place during the basic treatment step of the present process. A typical example of the acyl type of the amino-protecting group $R_1$, $R_2$ which is cleavable under the basic conditions is phthaloyl group. A typical example of the acyl type of the hydroxyl-protecting group Y which is cleavable under the basic conditions and which is suitable for the present process is an aminoalkanoyl group of the formula $—COCH(OH)(CH_2)_nNR_1R_2$ where $R_1$ and $R_2$ taken together form a phthaloyl group and $n$ is a whole number of 1 to 4. If the acyl-migration product (IV) so formed still contains the amino-protecting group and/or the hydroxyl-protecting group, such as an acyl group, which are in its nature cleavable under the basic conditions but which are remaining in the acyl-migration product (IV), further heating of the reaction mixture will ensure the complete removal of the residual amino- and hydroxyl-protecting groups from the acyl-migration product (IV) present therein, finally affording the desired product (II).

When the starting compound (III) contains a hydroxyl-protecting group Y of the other nature than the acyl or aminoacyl group as well as an amino-protecting group $R_1$, $R_2$ of the other nature than the acyl group, such hydroxyl-protecting group and amino-protecting group cannot be removed during the basic treatment step of the process, and it is necessary to further treat the acyl-migration product (IV) in a known manner so as to remove the hydroxyl-protecting group Y and the amino-protecting groups $R_1$, $R_2$ remaining in the acyl-migration product (IV). By the removal of the hydroxyl-protecting group or the amino-protecting group is herein meant the conversion of the hydroxyl-protecting group or the amino-protecting group into a hydrogen atom to regenerate the original, free hydroxyl or amino group. For instance, when the hydroxyl-protecting group Y is benzyl group and the amino-masking group $R_1$ and/or $R_2$ are or is such as alkyloxycarbonyl, aralkyloxycarbonyl or aryloxycarbonyl, particularly carbobenzoxy group in the starting compound (III), the acyl-migration product (IV) obtained still contains these hydroxyl-protecting group and amino-protecting groups remaining therein and must be further treated so as to remove the hydroxyl-protecting group and amino-protecting groups of these kinds. Procedures for the removal of these hydroxyl-protecting group and amino-protecting group are well known to the skilled in the art. Thus, when the amino-masking group is of an alkyloxycarbonyl group such as t-butoxycarbonyl, a cycloalkyloxycarbonyl group, or aryloxycarbonyl group or an arylidene group such as salicylidene group, the removal of this kind of the amino-masking group may be effected by subjecting to a moderate hydrolysis treatment with a weak acid such as aqueous trifluoroacetic acid, aqueous acetic acid and diluted aqueous hydrochloric acid. When the amino-masking groups is of an aralkyloxycarbonyl group such as benzyloxycarbonyl, the removal of this sort of the amino-masking group may be effected by subjecting to a hydrogenolysis treatment in the presence of a palladium-carbon catalyst or to a treatment with hydrobromic acid and acetic acid. The o-nitrophenoxyacetyl group as the amino-masking group may be removed by a reductive treatment. When the amino-masking group is phthaloyl group, the removal of phthaloyl group may efficiently be achieved by treating hydrolytically with hydrazine hydrate in solution in ethanol under heating.

When the hydroxyl-masking groups is of the acyl type such as alkanoyl and aroyl or ally, isopropylidene, cyclohexylidene, benzylidene, tetrahydropyranyl or methoxycyclohexyl, the removal of this acyl type of the hydroxyl-masking group may be accomplished by mild hydrolysis using diluted hydrochloric acid or aqueous acetic acid. When the hydroxyl-masking group is of such type as benzyl, the removal of this type of the hydroxyl-masking group may be achieved by catalytic hydrogenolysis in the presence of palladium on carbon.

The 6-0-((S)-α-hydroxy-ω-aminoacyl)-3', 4'-dideoxyneamine or -3', 4'-dideoxyribostamycin of the formula (III) which is used as the starting compound in the process of this invention may be prepared from 3', 4'-dideoxyneamine or 3', 4'-dideoxyribostamycin as the initial material in various ways. Thus, 3', 4'-dideoxyneamine or 3', 4'-dideoxyribostamycin is at first reacted with such a reagent which is commonly used in the prior art of peptide synthesis to introduce a known amino-protecting group into the four amino groups of the initial 3', 4'-dideoxyneamine or 3', 4'-dideoxyribostamycin. The protection or masking of the amino groups of the neamine or ribostamycin may conveniently be effected in a known manner, either by reacting an aldehyde such as acetaldehyde or benzaldehyde with the amino group to convert the latter into Schiff's base type of the group, or by an acylating, carboalkoxylating or carbobenzoxylating the amino groups of the initial material. To this end, for example, 3', 4'-dideoxyneamine or 3', 4'-dideoxyribostamycin may be reacted with acetyl chloride, ethyl chloroformate or benzyl chloroformate to prepare the tetra-N-acetyl derivative, the tetra-N-ethoxycarbonyl derivative or the tetra-N-carbobenzoxy derivative of the neamine or ribostamycin, respectively.

The tetra-N-acetyl derivative, tetra-N-ethoxycarbonyl derivative or tetra-N-carbobenzoxy derivative of 3', 4'-dideoxyneamine or 3', 4'-dideoxyribostamycin so prepared may subsequently be treated in a known manner so as to block all or parts of the hydroxyl groups other than the 6-hydroxyl group of said derivative with a known hydroxyl-protecting group such as an acyl, isopropylidene, cyclohexylidene, benzylidene or benzyl. The introduction of the hydroxyl-protecting group into all the hydroxyl groups other than the 6-hydroxyl group of said derivative may be achieved in a similar way to the preparation of tetra-N-carbobenzoxy-3', 4': 2'',3''-dicyclohexylidene-5''-O-(1-methoxycyclohexyl)-ribostamycin, as is described in the "Journal of Antibiotics" Vol. 25, No. 10, pages 613–616 (1972). The derivative having the protected hydroxyl groups so formed is then esterified by reacting with an (S)-α-hydroxy-ω-amino acid of the formula (V)

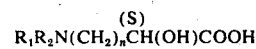

$$R_1R_2N(CH_2)_n\overset{(S)}{C}H(OH)COOH \qquad (V)$$

wherein $R_1$, $R_2$ are $n$ are as defined in the above or a functional derivative of this amino acid (V) in an anhydrous organic solvent in the presence of a dehydrating agent, to prepare 6-O-((S)-α-hydroxy-ω-aminoacyl derivative of 3', 4'-dideoxyneamine or 3', 4'-dideoxyribostamycin in which the neamine or ribostamycin molecule the four amino groups have been masked by the amino-protecting group and the hydroxyl groups also have been protected by the hydroxyl-protecting groups. When this 6-O-((S)-α-hydroxy-ω-aminoacyl derivative so prepared is then treated in a known manner so as to remove all the amino-protecting groups and, if desired, also all of the hydroxyl-protecting groups, there may be prepared the 6-O-((S)-α-hydroxy-ω-aminoacyl)-3', 4'-dideoxyneamine or -3', 4'-dideoxyribostamycin of the above formula (III) where $R_1$, $R_2$ and Y each is a hydrogen atom.

When an organic compound containing both amino group and hydroxyl group in the molecule thereof is intended to be acetylated preferentially at the hydroxyl group, it has been proposed that the protection of the amino group is done by protonating such amino group with a strong organic acid such as trifluoroacetic acid so as to protect said amino group, and then the hydroxyl group may be acetylated preferentially using a usual acetylation reagent such as acetyl chloride or acetic anhydride or mixed anhydrides (see J. Bello & J. R. Vinograd; "Journal of American Chemical Society" Vol. 78, page 1369 (1956)). Using this known method of protonating the amino group with a strong organic acid such as trifluoroacetic acid for the purpose of protecting the amino groups of the initial 3', 4'-dideoxyneamine or 3', 4'-dideoxyribostamycin, the 6-O-((S)-α-hydroxy-ω-aminoacyl)-3', 4'-dideoxyneamine or -3',4'-dideoxyribostamycin of the formula (III) may also be prepared in the following way: The 3', 4'-dideoxyneamine or 3', 4'-dideoxyribostamycin (the free base form) is dissolved in trifluoroacetic acid under ice-cooling and the resulting solution is admixed with ethyl ether to precipitate such a trifluoroacetic acid salt of 3', 4'-dideoxyneamine or 3', 4'-dideoxyribostamycin in which the four amino groups of the 3', 4'-dideoxyneamine or 3', 4'-dideoxyribostamycin molecule have each been protected with the trifluoroacetic acid molecule. This 3', 4' -dideoxyneamine or 3', 4'-dideoxyribostamycin trifluoroacetate so formed is then esterified or condensed with an (S)-α-hydroxy-ω-amino acid of the formula (V) in solution in an organic solvent such as dimethylformamide (DMF), acetone or tetrahydrofuran under ice-cooling and in the presence of a strong acid or a dehydrating agent such as dicyclohexylcarbodiimide. The acid of the formula (V) may conveniently be its functional derivative such as acid halide, azide derivative, active ester or mixed acid anhydride. In the reaction (esterification) of the 3', 4'-dideoxyneamine or 3', 4'-dideoxyribostamycin trifluoroacetate with the acid of the formula (V), all the hydroxyl groups, including the 6-hydroxyl group, of the 3', 4'-dideoxyneamine or 3', 4'-dideoxyribostamycin molecule are unblocked and are O-amino-acylated at random by the acid of the formula (V), so that there is formed a mixture of mono-O-aminoacylated and di-O-aminoacylated 3', 4'-dideoxyneamines (in the form of their trifluoroacetate) or a mixture of mono-O-aminoacylated to tetra-O-aminoacylated 3', 4'-dideoxyribostamycins (in the form of their trifluoroacetate). When this mixture of the O-aminoacylated 3', 4'-dideoxyneamine or 3', 4'-dideoxyribostamycin trifluoroacetates is neutralized with a base, there is given the mixed O-aminoacylated 3', 4'-dideoxyneamines or 3', 4'-dideoxyribostamycins which contain a 6-O-((S)-α-hydroxy-ω-aminoacyl)-3', 4'-dideoxyneamine or 3', 4'-dideoxyribostamycin of the formula (III). From the above-mentioned mixed O-aminoacylated 3', 4'-dideoxyneamines or 3', 4'-dideoxyribostamycins may be isolated the 6-O-((S)-α-hydroxy-ω -aminoacyl)-3', 4'-dideoxyneamine or -3', 4'-dideoxyribostamycin of the formula (III) by a chromatographic method using, for example, cellulose powder, silica gel or a molecular sieve consisting of a three-dimensional dextran network (commercially available under a trade name "Sephadex G-15", a product of Pharmacia Co., Sweden). However, the above-mentioned mixed O-aminoacylated 3', 4'-dideoxyneamines or 3', 4'-dideoxyribostamycins containing the 6-O-((S)-α-hydroxy-ω-aminoacyl)-3', 4'-dideoxyneamine or -3', 4'-dideoxyribostamycins as such may be immediately employed as the starting material for the process of this invention, before or after the trifluoroacetic acid is liberated therefrom by neutralizing with a base, as stated above. This is because the (S)-α-hydroxy-γ-aminoacyl substituent(s) on the other hydroxyl group(s) than the 6-hydroxyl group in these mixed O-aminoacylated product may be regarded as one of the hydroxyl-protecting group Y of the acyl type as stated before. When said mixed O-aminoacylated 3', 4'-dideoxyneamines or 3', 4'-dideoxyribostamycins are subjected to the action of the basic medium in the process of this invention, there is formed the desired 1-N-((S)-α-hydroxy-ω-aminoacyl)-3', 4'-dideoxyneamine or -3', 4'-dideoxyribostamycin of the formula (II) as the sole acyl-migration product, because the migration of the (S)-α-hydroxy-ω-aminoacyl substituent from the hydroxyl group to the amino group cannot take place except that from the 6-hydroxyl group to the 1-amino group as long as the 3', 4'-dideoxyneamine or 3', 4'-dideoxyribostamycin (III) is concerned with as the starting compound in the present process. The N-aminoacylation product may be precipitated from the reaction mixture by concentration of the latter and filtered out and dissolved in water to prepare an aqueous solution of them at pH of about 8. This solution may then be subjected to a chromatographic separation in a column of CM-Sephadex C-25 (ammonium form) to isolate the desired 1-N-((S)-α-hydroxy-ω-aminoacyl)-3', 4'-dideoxyneamine or -3', 4'-dideoxyribostamycin of the formula (II). Active fractions of the eluate issued from the column and containing the 1-N-((S)-α-hydroxy-ω-aminoacyl)-3', 4'-dideoxyneamine or -3', 4'-dideoxyribostamycin can be detected by an oxidation test with periodic acid, as the presence of an 1-N-acyl substituent is detectable by said test (see "Tetrahedron Letters", Vol. 28, pages 2624–2628 (1971)).

when the 3', 4'-dideoxyneamine or 3', 4'-dideoxyribostamycin trifluoroacetate is esterified by reacting with an (S)-α-hydroxy-ω-amino acid derivative of the formula (V), it has been found preferable that 1 molar proportion of the former is brought about into contact with 3–7 molar proportions of the latter at a temperature of 50°–100°C. When the compound of the formula (III) in its trifluoroacetate form is directly subjected to the action of the basic medium which may be a solution of hydrazine in an aqueous ethanol, the migration of the 6-O-(S)-α-hydroxy-ω-aminoacyl substituent from the 6-hydroxyl group to the 1-amino group takes place concurrently with or after the liberation of the trifluoroacetic acid from the starting compound (III) trifluoroacetate occurs. In this case when the compound (III) trifluoroacetate is directly subjected to the action of the basic medium, therefore, it is virtual that the formation of the product (IV) from the compound (III) trifluoroacetate takes place again via the compound (III) itself formed in site of the reaction mixture.

The principal route of producing the final product of the formula (II) starting from 3',4'-dideoxyneamine or 3',4'-dideoxyribostamycin (I) according to the present invention may be represented schematically by the following equation:

groups from the product are omitted from the representation.

Among the amino acid of the formula (V) which is used in the process, an (S)-α-hydroxy-ω-amino acid of the formula (V) where $R_1$ and $R_2$ each is not the hydrogen atom may conveniently be an (S)-α-hydroxy-ω-N-phthalimido acid or (S)-α-hydroxy-ω-N-carbobenzox-

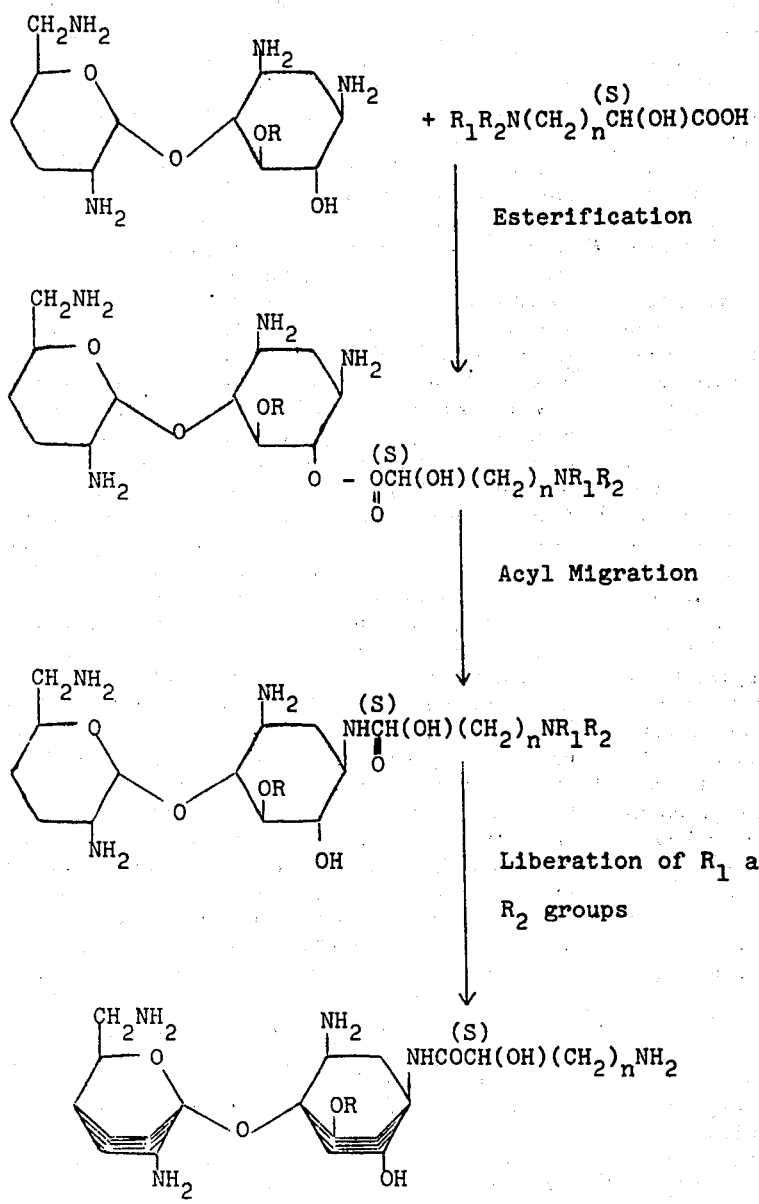

if the reactions for introducing the amino-protecting groups and the hydroxyl-protecting groups into the initial 3',4'-dideoxyneamine or 3',4'-dideoxyribostamycin, the presence of the amino-protecting and hydroxyl-protecting groups in the reagents and in the intermediate products, and the reactions for removing the amino-protecting groups and hydroxyl-protecting yamino acid. An (S)-α-hydroxy-ω-N-phthalimido acid of the formula

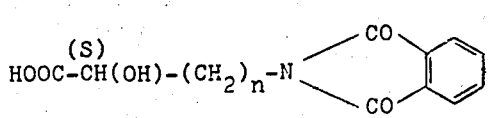

may be prepared by reacting a hydrochloride of an (S)-α-,ω-diamino acid of the formula

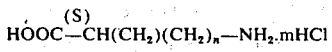

wherein *m* is a whole number of 1 or 2, with a basic copper carbonate in an alkaline aqueous solution to form the copper carboxylate, reacting this copper carboxylate with N-carboethoxyphthalimide to form a copper salt of (S)-α-amino-ω-N-phthalimido acid of the formula

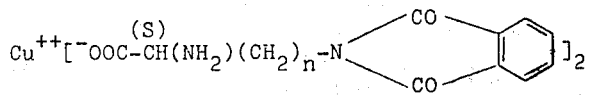

treating this copper salt with diluted hydrochloric acid in methanol to give the corresponding (S)-α-amino-ω-N-phthalimido acid hydrochloride and then reacting this hydrochloride with sodium nitrite in aqueous acetic acid to produce the desired (S)-α-hydroxy-ω-N-phthalimido acid.

As the amino acid of the formula (V), it is, of course, possible to use such an (S)-α-hydroxy-ω-amino acid (V) where $R_1$ and $R_2$ each is a hydrogen atom or a known amino-protecting group other than the aforesaid phthaloyl group. For preparation of an (S)-α-hydroxy-ω-amino acid (V) in which $R_1$ is a hydrogen atom and $R_2$ is independently an acyl group, alkyloxycarbonyl group, aralkyloxycarbonyl or aryloxycarbonyl group, for example, by reacting an α-hydroxy-ω-amino acid of the formula

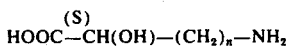

wherein *n* is a whole number of 1 to 4, with an acyl chloride of the formula

wherein $R_3$ is a group such that the $R_3CO$ group forms the group $R_2$ which is an acyl group such as acetyl or benzoyl, in a dry organic solvent such as methanol, or with an alkyloxycarbonyl, aralkyloxycarbonyl or aryloxycarbonyl chloride of the formula

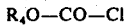

wherein $R_4$ is a group such that the $R_4O$—CO— group forms the $R_2$ group which is an alkyloxycarbonyl, aralkyloxycarbonyl or aryloxycarbonyl group such as butoxycarbonyl, benzyloxycarbonyl or phenoxycarbonyl, in a suitable solvent such as ethyl alcohol or acetone under neutral or basic conditions in a way well known in the prior art of peptide synthesis.

This invention is now illustrated with reference to the following Examples to which this invention is not limited in any way.

EXAMPLE 1 a. 831 Mg of 3′, 4′-dideoxyneamine (the free base form) was added into 8.3 ml of trifluoroacetic acid under water-cooling. After 1 hour later, the resulting solution was admixed with 100 ml of ethyl ether, and there was formed the precipitate (1,430 mg) of the 3′, 4′-dideoxyneamine trifluoroacetate which was then removed by filtration. 745 Mg of the 3′, 4′-dideoxyneamine trifluoroacetate was admixed with 807 mg of (S)-α-hydroxy-γ-N-phthalimido-n-butyric acid in the powdery solid state, and the resulting mixture was dissolved in 20 ml of a liquid mixture of (10:1) tetrahydrofurandimethylformamide, to which was subsequently added 5.5 ml of a solution of 1,530 mg of dicyclohexylcabodiimide in tetrahydrofuran under ice-cooling. The resultant admixture was agitated for 1 hour under ice-cooling and for further 2 hours at room temperature to effect the esterification. 0.4 Ml of glacial acetic acid was added to the reaction mixture to decompose the excess of the dicyclohexylcarbodiimide reagent. The reaction mixture was allowed to stand at room temperature overnight. The precipitate of dicyclohexylurea formed was filtered off and the filtrate was concentrated to dryness to give 1,530 mg of a solid product comprising 6-O-((S)-α-hydroxy-γ-N-phthalimido-n-butyryl)-3′, 4′-dideoxyneamine trifluoroacetate together with the other mixed O-((S)-α-hydroxy-γ-N-phthalimido-n-butyryl)-3′, 4′-dideoxyneamines (in the form of their trifluoroacetates).

b. This solid product (1,500 mg) comprising the 6-O-((S)-α-hydroxy-γ-N-phthalimido-n-butyryl)-3′, 4′-dideoxyneamine trifluoroacetate was dissolved in 35 ml of a liquid mixture of aqueous 80% hydrazine hydrate and ethanol (1:10), and the resulting solution was heated for 1.5 hours on a water-bath at 83°C to effect the liberation of the trifluoroacetic acid, the acyl-migration reaction and the removal of the phthaloyl group, giving 6-N-((S)-α-hydroxy-γ-amino-n-butyryl)-3′, 4′-dideoxyneamine together with the other mixed N-((S)-α-hydroxy-γ-amino-n-butyryl)-3′, 4′-dideoxyneamines. The reaction mixture was then concentrated to dryness and the solid residue was extracted with 50 ml of water. The insoluble matter was filtered off and the aqueous solution (the filtrate) was adjusted to pH 8.0 by addition of diluted sulfuric acid. This aqueous solution was passed into a column of 15 ml of CM-Sephadex C-25 (the ammonium form)(CM-Sephadex C-25 is such a known molecular-sieve material essentially consisting of a three-dimentional gel network of dextran bearing carboxymethyl radicals as the weakly acidic, ion-exchanger functional group). After the column was washed with 50 ml of water and then with 200 ml of 0.1N aqueous ammonia, the column was eluted using 0.2N aqueous ammonia. The eluate was collected in 10 ml fractions. Such fractions of the eluate containing the un-reacted starting material was discarded, and such active fractions Nos. 18–34 were combined together and concentrated to dryness, affording 156.3 mg of 1-N-((S)-α-hydroxy-γ-amino-n-butyryl)-3′, 4′-dideoxyneamine.

| Elemental analysis | |
|---|---|
| Found: | C 46.31, H 8.48, N 16.59% |
| Calculated for $C_{16}H_{33}N_5O_8 \cdot H_2O$ | C 46.93, H 8.62, N 17.10% |

This product showed an optical rotation $[\alpha_D^{23} +37°$ (c = 1.2, $H_2O$) and an $R_{3,4'}$ -dideoxyneamine of 0.47 in a paper chromatography using (6:4:1:3) n-butanol-pyridine-acetic acid-water as the development solvent. The figure of $R_{3,4'}$ -dideoxyneamine designates the ratio of the distance of migration of the spot of the 1-N-((S)-α-hydroxy-γ-amino-n-butyryl)-3', 4'-dideoxyneamine product to that of 3', 4'-dideoxyneamine The product did not show a clear melting point but decomposed at about 190°C. The product had the minimum inhibitory concentrations (MIC.) to the growth of various microorganisms as shown in Table 1 below.

Table 1

| Test Microorganism | Incubation medium | MIC. (mcg/ml) |
|---|---|---|
| Escherichia coli NIHJ | Nutrient agar | 3.12 |
| Escherichia coli K-12 | '' | 3.12 |
| Staphylococcus aureus FDA 209P | '' | 3.12 |
| Escherichia coli K-12 ML 1410 R81 | '' | 12.5 |
| Pseudomonas aeruginosa A3 | '' | 12.5 |
| Pseudomonas aeruginosa No.12 | '' | 6.25 |

EXAMPLE 2 a. 605 mg of 3', 4'-dideoxyribostamycin (the free base form) was added into 25 ml of trifluoroacetic acid under ice-cooling, and the mixture was allowed to stand for 2 hours at room temperature for dissolution. The resulting solution was admixed with 200 ml of ethyl ether and cooled to precipitate 1,201 mg of 3', 4'-dideoxyribostamycin trifluoroacetate which was then removed by filtration. A portion (1,005 mg) of this trifluoroacetate product was taken and dissolved in 12.5 ml of tetrahydrofuran together with 803 mg of (S)-α-hydroxy-γ-N-phthalimido-n-butyric acid. The solution so obtained was cooled with ice and then admixed with an ice-cooled solution of 1.8 g of dicyclohexylcarbodiimide in 7 ml of tetrahydrofuran under ice-cooling and stirring. The admixture was stirred for 3 hours at room temperature and then admixed with 0.4 ml of glacial acetic acid to decompose the excess of dicyclohexylcarbodiimide reagent. The admixture was allowed to stand overnight, during which the insoluble dicyclohexylurea so formed precipitated. This insoluble solid was filtered off and the filtrate was concentrated to dryness, giving 1,735 mg of a solid product comprising 6-O-((S)-α-hydroxy-γ-N-phthalimido-n-butyryl)-3', 4'-dideoxyribostamycin trifluoroacetate together with the other mixed O-((S)-α-hydroxy-γ-N-phthalimido-n-butyryl)-3', 4'-dideoxyribostamycins (in the form of their trifluoroacetates).

This solid product (1,700 mg) comprising the 6-O-((S)-α-hydroxy-γ-N-phthalimido-n-butyryl)-3', 4'-dideoxyribostamycin trifluoroacetate was dissolved in 40 ml of a liquid mixture of aqueous 80% hydrazine hydrate and ethanol (1:10), and the resulting solution was heated for 1.5 hours on a water-bath at 83°C to effect the liberation of the trifluoroacetic acid, the acyl-migration reaction and the removal of the phthaloyl group, so that there was produced 6-N-((S)-α-hydroxy-γ-amino-n-butyryl)-3', 4'-dideoxyribostamycin together with the other mixed N-((S)-α-hydroxy-γ-amino-n-butyryl)-3', 4'-dideoxyribostamycins. The liquid reaction solution was concentrated to dryness and the solid residue so obtained was extracted with 50 ml of water. The insoluble matter was filtered off and the aqueous solution (the filtrate) was adjusted to pH 8.0 by addition of diluted sulfuric acid. This aqueous solution was passed into a column of 15 ml of CM-Sephadex C-25 (a registered trademark) (the ammonium form). After the column was washed with 50 ml of water and then with 200 ml of 0.1N aqueous ammonia, the column was eluted using 0.2N aqueous ammonia. The eluate was collected in 10 ml fractions. Such fractions of the eluate containing the un-reacted starting material were discarded, and such fractions Nos. 14-30 were combined together and concentrated to dryness, affording 238.2 mg of 1-N-((S)-α-hydroxy-γ-amino-n-butyryl)-3', 4'-dideoxyribostamycin.

Elemental analysis
| | |
|---|---|
| Found: | C 46.01, H 7.89, N 12.71% |
| Calculated for $C_{21}H_{41}N_5O_{10}\cdot H_2O$: | C 46.57, H 8.00, N 12.93% |

This product showed an optical rotation $[\alpha]_D^{23}$ +27° (c = 1.2, $H_2O$) and an $R_{3',4'}$ -dideoxyribostamycin of 0.46 in a paper chromatography using (6:4:1:3) n-butanolpyridine-acetic acid-water as the development solvent. The figure of $4_{3',4'}$ -dideoxyribostamycin designates the ratio of the distance of migration of the spot of the 1-N-((S)-α-hydroxy-γ-amino-n-butyryl)-3', 4'-dideoxyribostamycin to that of 3', 4'-dideoxyribostamycin. The product did not show a clear melting point but decomposed at about 190°C. The product had the minimum inhibitory concentrations (MIC.) to the growth of various microorganisms as shown in Table 2 below.

Table 2

| Test Microorganism | Incubation medium | MIC. (mcg/ml) |
|---|---|---|
| Escherichia coli NIHJ | Nutrient agar | 1.56 |
| Escherichia coli K-12 | '' | 1.56 |
| Staphylococcus aureus FDA 209P | '' | 1.56 |
| Escherichia coli K-12 ML 1410 R81 | '' | 3.12 |
| Pseudomonas aeruginosa A3 | '' | 6.25 |
| Pseudomonas aeruginosa No. 12 | '' | 6.25 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages conditions.

What is claimed is:

1. A process for the production of a 1-N-((S)-α-hydroxy-ω-aminoalkanoyl-3', 4'-dideoxyneamine or -3', 4'-dideoxyribostamycin of the formula

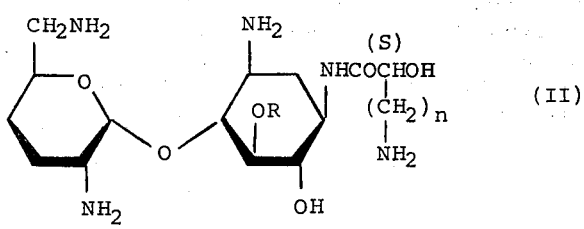

wherein R is a hydrogen atom or β-D-ribofuranosyl group of the formula

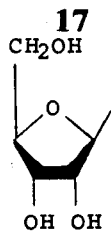

and *n* is a whole number of 1 to 4, which consists essentially of the following four steps:
a. reacting 3', 4'-dideoxyneamine or 3', 4'-dideoxyribostamycin with trifluoroacetic acid to prepare 3', 4'-dideoxyneamine tetra-trifluoroacetate or 3', 4'-dideoxyribostamycin tetra-trifluoroacetate;
b. esterifying at random the hydroxyl groups of the 3', 4'-dideoxyneamine tetra-trifluoroacetate or 3', 4'-dideoxyribostamycin tetra-trifluoroacetate by reacting with an (S)-α-hydroxy-ω-phthalimidoalkanoic acid of the formula $$R_1R_2N-(CH_2)_n-CH(OH)-COOH$$

wherein $R_1$ and $R_2$ taken together form a phthaloyl group and *n* is a whole number of 1 to 4, to prepare a mixture of differently O-(S)-α-hydroxy-ω-phthalimidoalkanoylated 3', 4'-dideoxyneamine tetra-trifluoroacetates or 3', 4'-dideoxyribostamycin tetra-trifluoroacetete;
c. treating the whole mixture of said differently O-(S)-α-hydroxy-ω-phthalimidoalkanoylated products with aqueous hydrazine or an aqueous alkali metal hydroxide, to effect the liberation of trifluoroacetic acid, the removal of the phthaloyl group and the migration of the (S)-α-hydroxy-ω-aminoalkanoyl group from the 6-hydroxyl group to the 1-amino group of the neamine or ribostamycin moiety simultaneously, whereby the desired 1-N-((S)-α-hydroxy-ω-aminoalkanoyl)-3', 4'-dideoxyneamine or -3', 4'-dideoxyribostamycin is formed, and
d. recovering said desired 1-N-((S)-α-hydroxy-ω-aminoalkanoyl)-3',4'-dideoxyneamine or -3',4'-dideoxyribostamycin.

2. A process as claimed in claim 1 in which the step (b) of treating the mixture of the differently O-alkanoylated products is carried out with aqueous hydrazine at a temperature of 50°–100°C in solution in an alkanol of 1–4 carbon atoms using the hydrazine in an amount sufficient to make the solution basic.

* * * * *